(12) United States Patent
Yousefian

(10) Patent No.: US 11,793,666 B1
(45) Date of Patent: Oct. 24, 2023

(54) INTRA-ORAL SNORE AND SLEEP APNEA TREATMENT APPLIANCE

(71) Applicant: Joseph Yousefian, Bellevue, WA (US)

(72) Inventor: Joseph Yousefian, Bellevue, WA (US)

( * ) Notice: Subject to any disclaimer, the term of this patent is extended or adjusted under 35 U.S.C. 154(b) by 11 days.

(21) Appl. No.: 17/722,958

(22) Filed: Apr. 18, 2022

Related U.S. Application Data

(60) Provisional application No. 63/175,750, filed on Apr. 16, 2021.

(51) Int. Cl.
*A61F 5/56* (2006.01)
*B33Y 80/00* (2015.01)

(52) U.S. Cl.
CPC .............. *A61F 5/566* (2013.01); *B33Y 80/00* (2014.12)

(58) Field of Classification Search
CPC ...... A61F 5/56; A61F 5/566; A61F 2005/563; A61C 7/08; A61C 7/36; A63B 71/085; A63B 71/086
See application file for complete search history.

(56) References Cited

U.S. PATENT DOCUMENTS

| | | | |
|---|---|---|---|
| 4,433,956 A | 2/1984 | Witzig | |
| 4,988,291 A | 1/1991 | Grummons | |
| 5,158,451 A | 10/1992 | Pourcho | |
| 5,683,244 A | 11/1997 | Truax | |
| 5,794,627 A * | 8/1998 | Frantz | A61F 5/566 128/859 |
| 6,976,838 B1 | 12/2005 | Keles | |
| 7,121,824 B2 | 10/2006 | Keles | |
| 7,712,468 B2 | 5/2010 | Hargadon | |
| 8,127,769 B2 * | 3/2012 | Walker | A61F 5/566 433/140 |
| 8,529,252 B2 | 9/2013 | Bukhary | |
| 8,821,155 B2 | 9/2014 | Mitani | |
| 8,833,374 B2 | 9/2014 | Fallon et al. | |
| 8,881,733 B1 * | 11/2014 | Harkins | A61C 7/08 128/860 |
| 9,138,341 B2 | 9/2015 | Greenburg | |
| 10,959,875 B2 | 3/2021 | Yousefian | |

(Continued)

FOREIGN PATENT DOCUMENTS

| | | |
|---|---|---|
| AU | 2004277278 | 4/2005 |
| DE | 19945444 | 10/2002 |
| WO | 2020210336 | 10/2020 |

*Primary Examiner* — Camtu T Nguyen
(74) *Attorney, Agent, or Firm* — Kolitch Romano Dascenzo Gates LLC

(57) ABSTRACT

A method of providing a patient with a dental appliance adapted to treat sleep apnea by touching the front lower dentition, thereby stimulating the mechanoreceptor reflex. In the method, the patient is provided with a temporary appliance, having an upper portion adapted to engage with upper teeth of the patient; a lower portion, adapted to touch lower teeth of the patient; a user accessible adjustment actuator, which when moved in a first direction advances the lower portion relative to the upper portion, and when moved in a second direction retracts the lower portion relative to the upper portion. The patient is directed to adjust the actuator, and thereby the appliance, as needed to treat sleep apnea, thereby creating an adjusted appliance. Finally, an adjusted appliance is received from the patient and a permanent appliance is produced based on the adjusted appliance.

17 Claims, 5 Drawing Sheets

(56) References Cited

U.S. PATENT DOCUMENTS

| | | | |
|---|---|---|---|
| 11,033,421 B1 | 6/2021 | Davis | |
| 2008/0060659 A1 | 3/2008 | Bonato et al. | |
| 2010/0261130 A1 | 10/2010 | Williams | |
| 2010/0261133 A1 | 10/2010 | Lax | |
| 2013/0068235 A1 | 3/2013 | Makower | |
| 2014/0090652 A1 | 4/2014 | Hakimi | |
| 2014/0190490 A1 | 7/2014 | Walker et al. | |
| 2014/0326253 A1 | 11/2014 | Baratier et al. | |
| 2017/0000643 A1* | 1/2017 | Gelb | A61F 5/566 |
| 2019/0159873 A1 | 5/2019 | Kaveh | |
| 2020/0268546 A1 | 8/2020 | Radmand | |
| 2021/0267721 A1 | 9/2021 | Simonetti | |

* cited by examiner

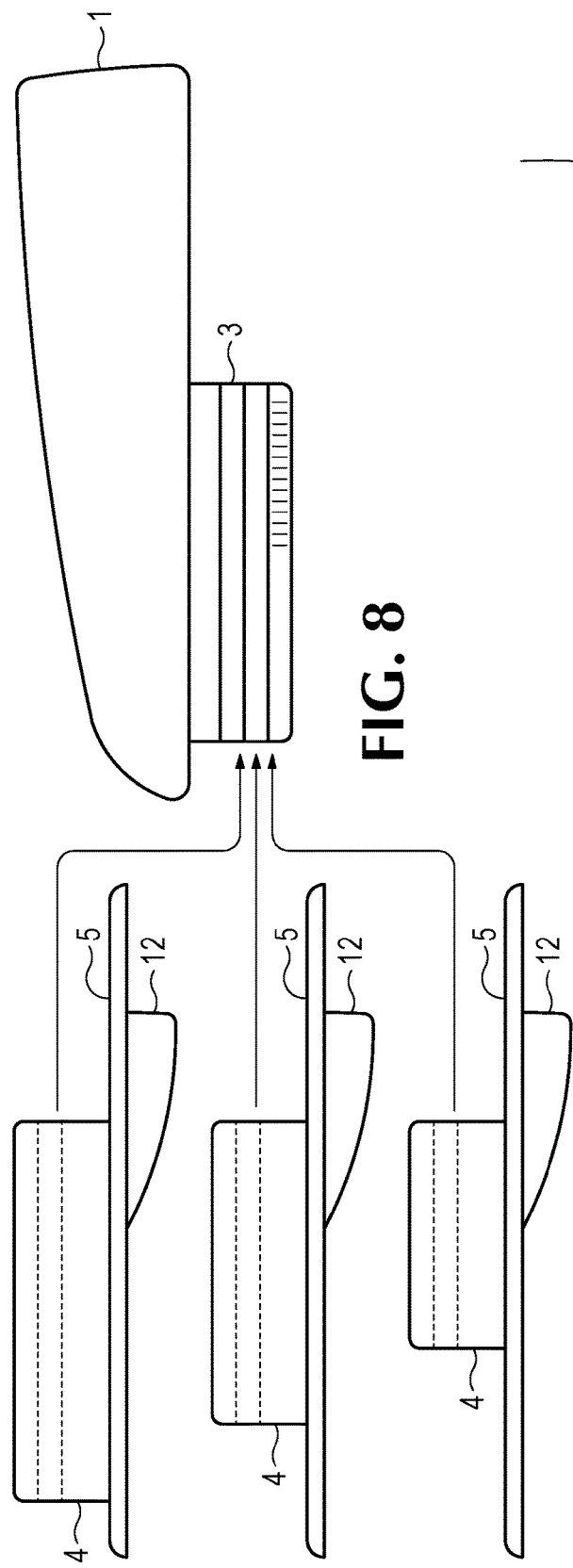
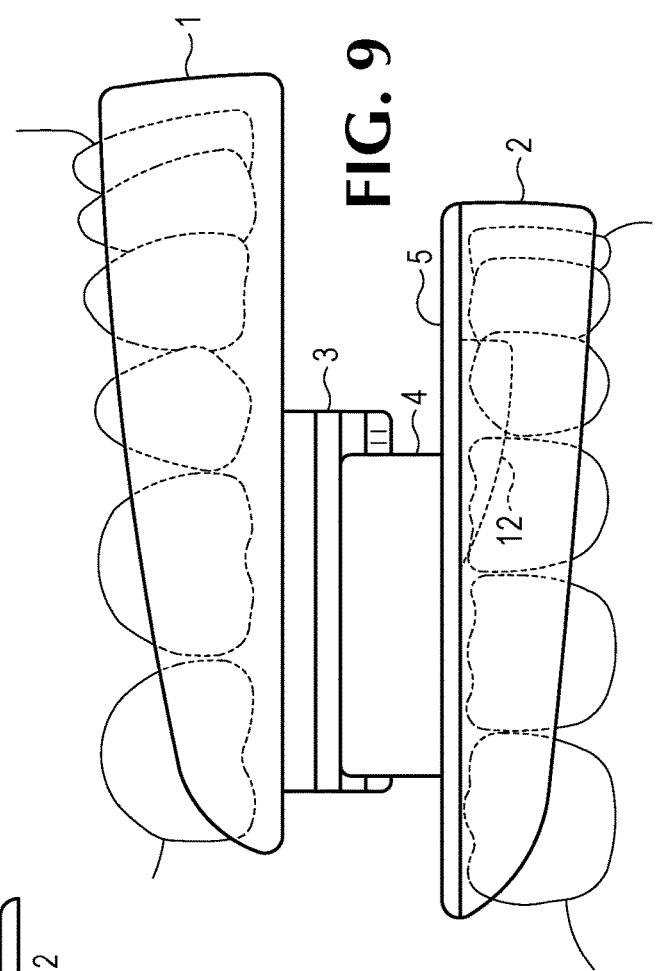

INTRA-ORAL SNORE AND SLEEP APNEA TREATMENT APPLIANCE

RELATED APPLICATION

This application claims priority from provisional application 63/175,750, filed Apr. 16, 2021, which is hereby fully incorporated, as if fully set forth herein.

BACKGROUND OF THE INVENTION

Although many devices for treating sleep apnea exist in the marketplace, there is still a need for an improved device to serve this function. Currently there is a divide between expensive devices that are prepared by a dental professional, versus mass market devices that are more easily within financial reach of many patients but are not customized for the mouth of the patient, thereby not serving their function as well as would a more expensive custom-made piece. Also, many currently available treatment devices have a tendency to force the mouth into a position in which the airway of the patient is opened, thereby causing discomfort as the sleep apnea is treated.

SUMMARY

The following embodiments and aspects thereof are described and illustrated in conjunction with systems, tools, and methods which are meant to be exemplary and illustrative, not limiting in scope. In various embodiments, one or more of the above-described problems have been reduced or eliminated, while other embodiments are directed to other improvements.

In a first separate aspect, the present invention may take the form of a method of providing a patient with a dental appliance adapted to treat sleep apnea by touching the front lower dentition, thereby stimulating the mechanoreceptor reflex. In the method, the patient is provided with a temporary appliance, having an upper portion adapted to engage with upper teeth of the patient; a lower portion, adapted to touch lower teeth of the patient; a user accessible adjustment actuator, which when moved in a first direction advances the lower portion relative to the upper portion, and when moved in a second direction retracts the lower portion relative to the upper portion. The patient is directed to adjust the actuator, and thereby the appliance, as needed to treat sleep apnea, thereby creating an adjusted appliance. Finally, an adjusted appliance is received from the patient and a permanent appliance is produced based on the adjusted appliance.

In a second separate aspect, the present invention may take the form of a dental appliance adapted to treat sleep apnea in a patient, and having an upper portion adapted to engage with the upper teeth of the patient and a lower portion, adapted to engage with the lower teeth of the patient. Further included in the appliance is a reflex-inducing piece, supported by the upper portion, and having a downward projection adapted to contact the lower front dentition of a human patient, thereby inducing the mechanoreceptor reflexes to advance the lower jaw and a reflex-inducing piece movement assembly, including a patient accessible actuator, for moving the reflex-inducing piece alternately forward and backward, as chosen by the patient.

In a third separate aspect, the present invention may take the form of a dental appliance adapted to treat sleep apnea in a patient, and having an upper portion adapted to engage with the upper teeth of the human patient and a lower portion, adapted to engage with the lower teeth of a human patient. Further included in the appliance is a reflex-inducing piece, supported by the upper portion, and having a downward projection adapted to contact the lower front dentition of a human patient, thereby inducing the mechanoreceptor reflexes to advance the lower jaw. Also, three soft forms, arranged in a triangle, provide cushioning between the lower portion and the reflex-inducing piece.

BRIEF DESCRIPTION OF DRAWINGS

Various embodiments of the invention are disclosed in the following detailed description and accompanying drawings.

FIG. 8 is a side view illustration of an alternate embodiment of a snore and sleep apnea treatment dental appliance, in which a reflex-inducing piece is chosen from a set of differing reflex-inducing pieces.

FIG. 9 is a side view of the appliance of FIG. 8, assembled with a chosen reflex-inducing piece and deployed into contact with human dentition.

DETAILED DESCRIPTION AND EMBODIMENTS

Figure 1:
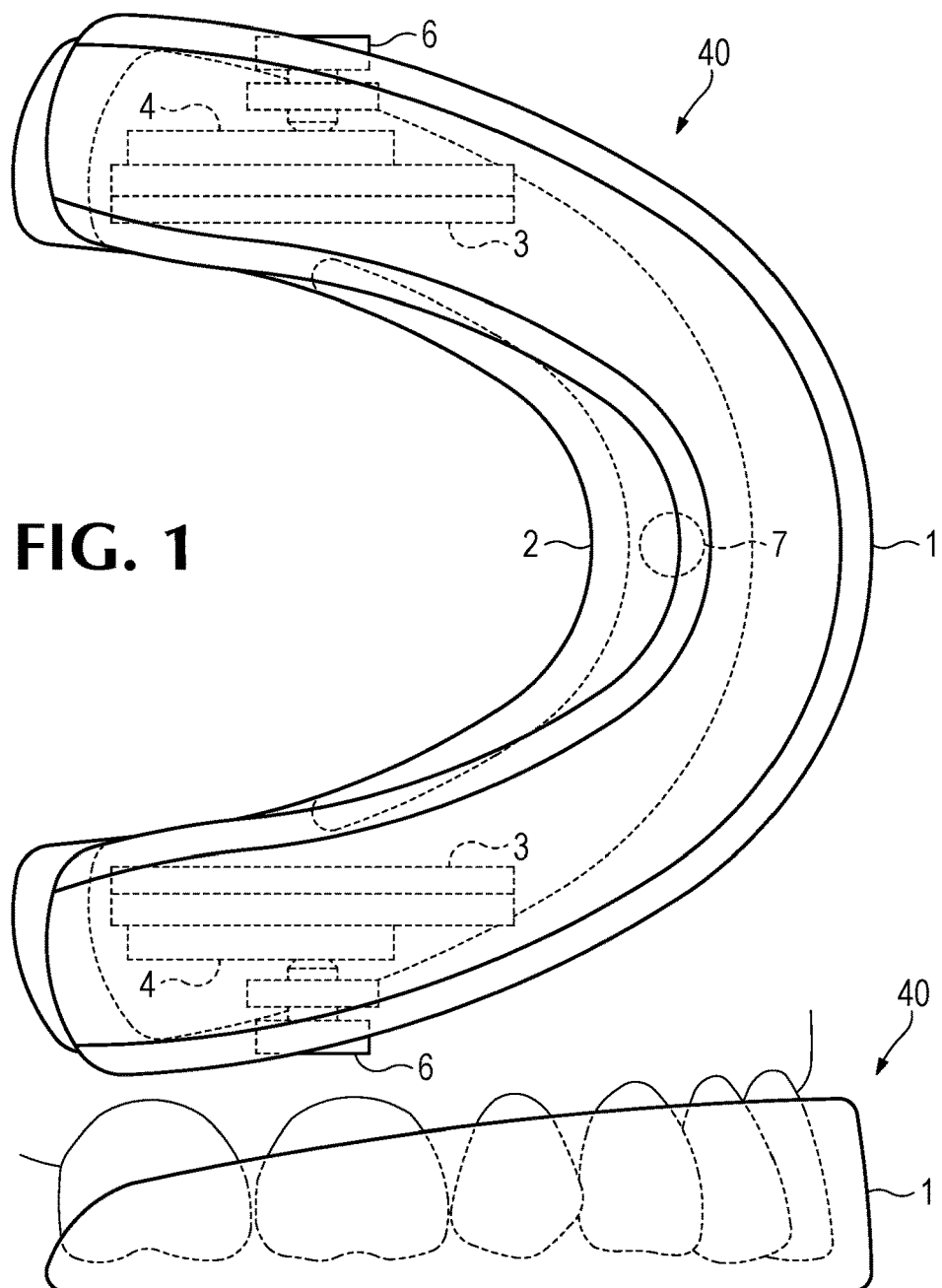
FIG. 1 is a top view of the snore and sleep apnea treatment dental appliance, according to the present invention, in a first configuration.
Figure 2:
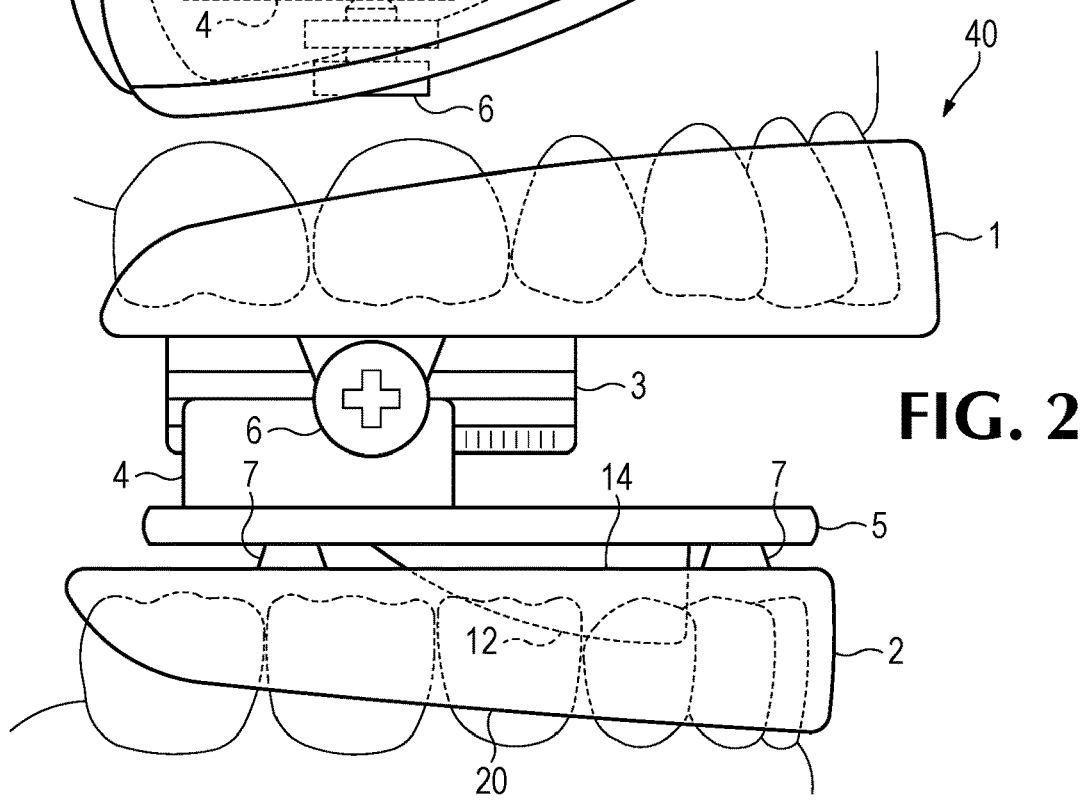
FIG. 2 is a side view of the dental appliance of FIG. 1, in the first configuration.
Figure 3:
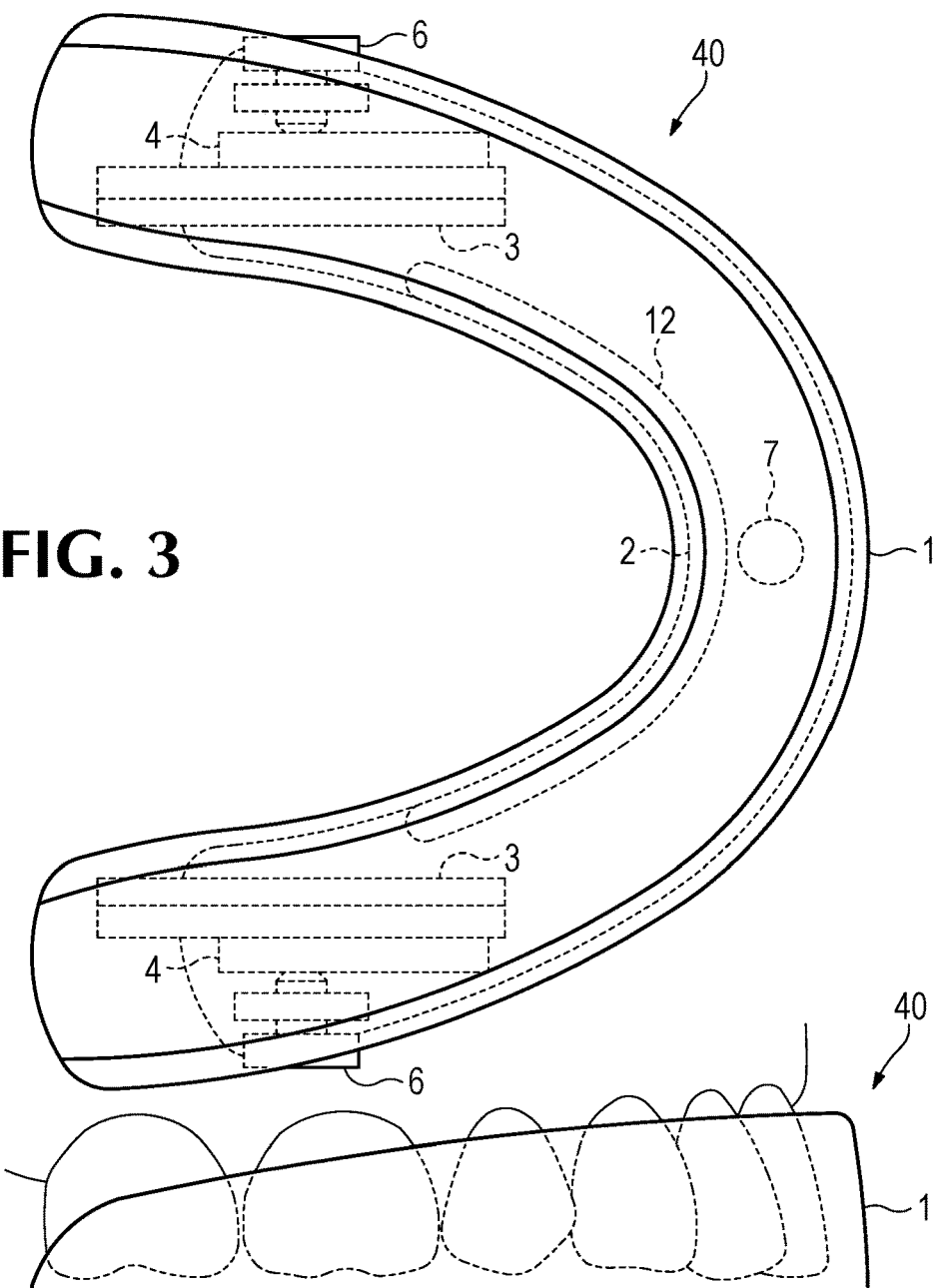
FIG. 3 is a top view of the dental appliance of FIG. 1, in a second configuration.
Figure 4:
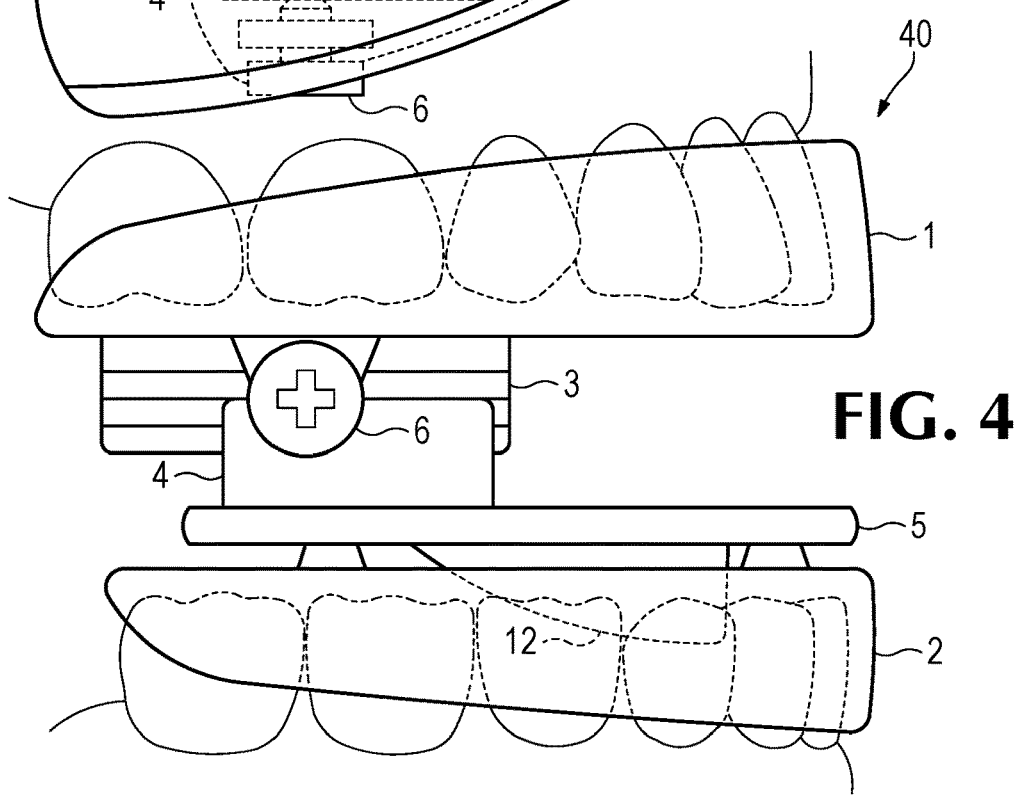
FIG. 4 is a side view of the dental appliance of FIG. 1, in the second configuration.
Figure 5:
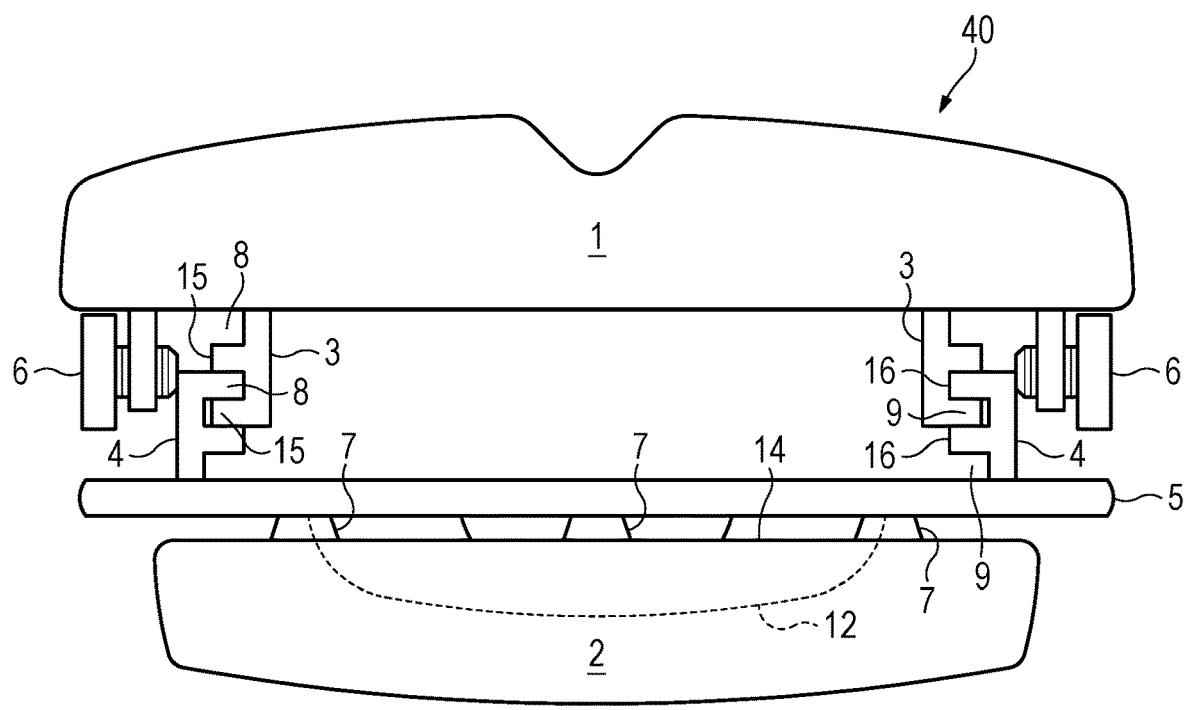
FIG. 5 is a front view of the dental appliance of FIG. 1.
Figure 6:
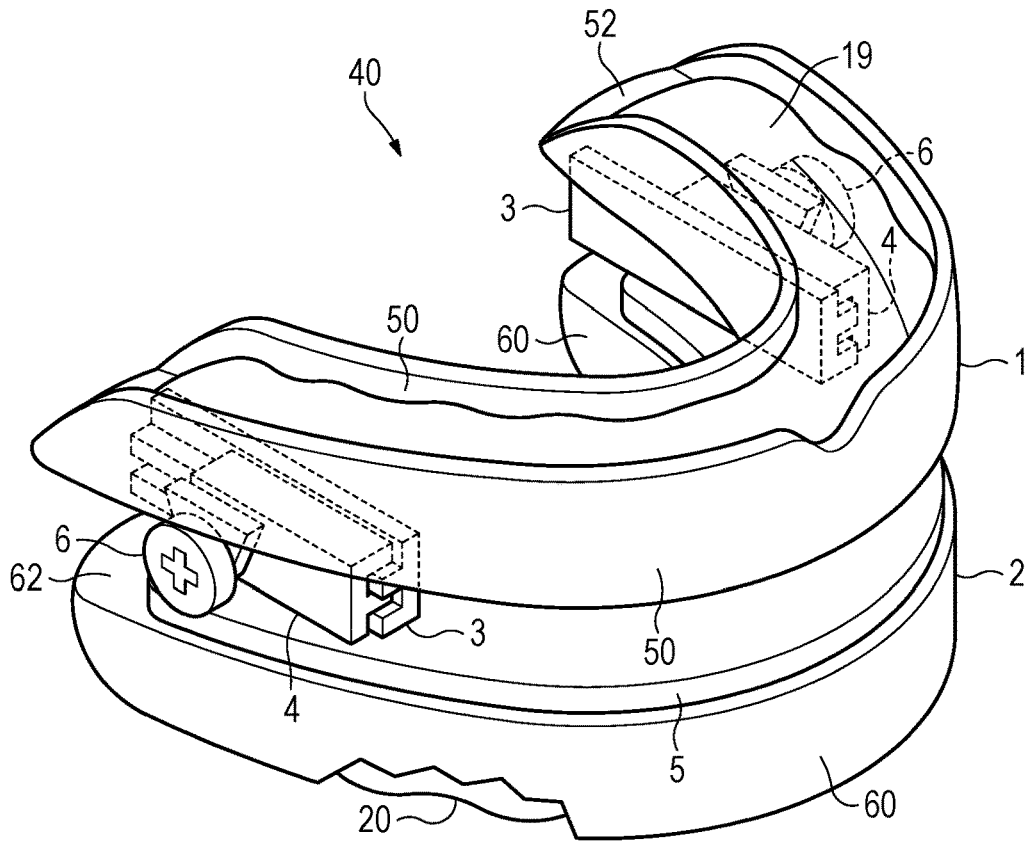
FIG. 6 is a side-top isometric view of the dental appliance of FIG. 1, in the second position.

The following is a detailed description of exemplary embodiments to illustrate the principles of the invention. The embodiments are provided to illustrate aspects of the invention, but the invention is not limited to any embodiment. The scope of the invention encompasses numerous alternatives, modifications and equivalent; it is limited only by the claims.

Definition: In the context of this application, "dentition" refers to both teeth and gums.

Numerous specific details are set forth in the following description in order to provide a thorough understanding of the invention. However, the invention may be practiced according to the claims without some or all of these specific details. For the purpose of clarity, technical material that is known in the technical fields related to the invention has not been described in detail so that the invention is not unnecessarily obscured.

To assist the description of the scope and its components the coordinate terms such as "upper" and "lower" are used to describe the disclosed embodiments. The terms are used consistently with the description of the exemplary applications and are in reference to the mouth of a user. In other words, "upper" relates to the upper part of the mouth and "lower" to the lower part of the mouth.

Referring to FIGS. 1-7, an oral appliance 40 for treating sleep apnea is shown. Appliance 40 consists of an upper plate compartment 1 (also referenced as "upper portion") and a lower plate compartment 2 (also referenced as "lower portion"). Further a reflex-inducing piece 5 is engaged to upper portion 1, by way of the engagement of a reflex-inducing piece sliding assembly 4 to an upper portion engagement assembly 3. By means of the engagement of assembly 4 to assembly 3, piece 5 can be slid forward and backward relative to upper portion 1 and locked in place by locking pin 6 (also referenced as "adjustment nub"). The portion of piece 5 which may be grasped by a patient and pulled or pushed, together with locking pin 6, is considered a user accessible adjustment actuator for the purposes of this application.

Figure 7:
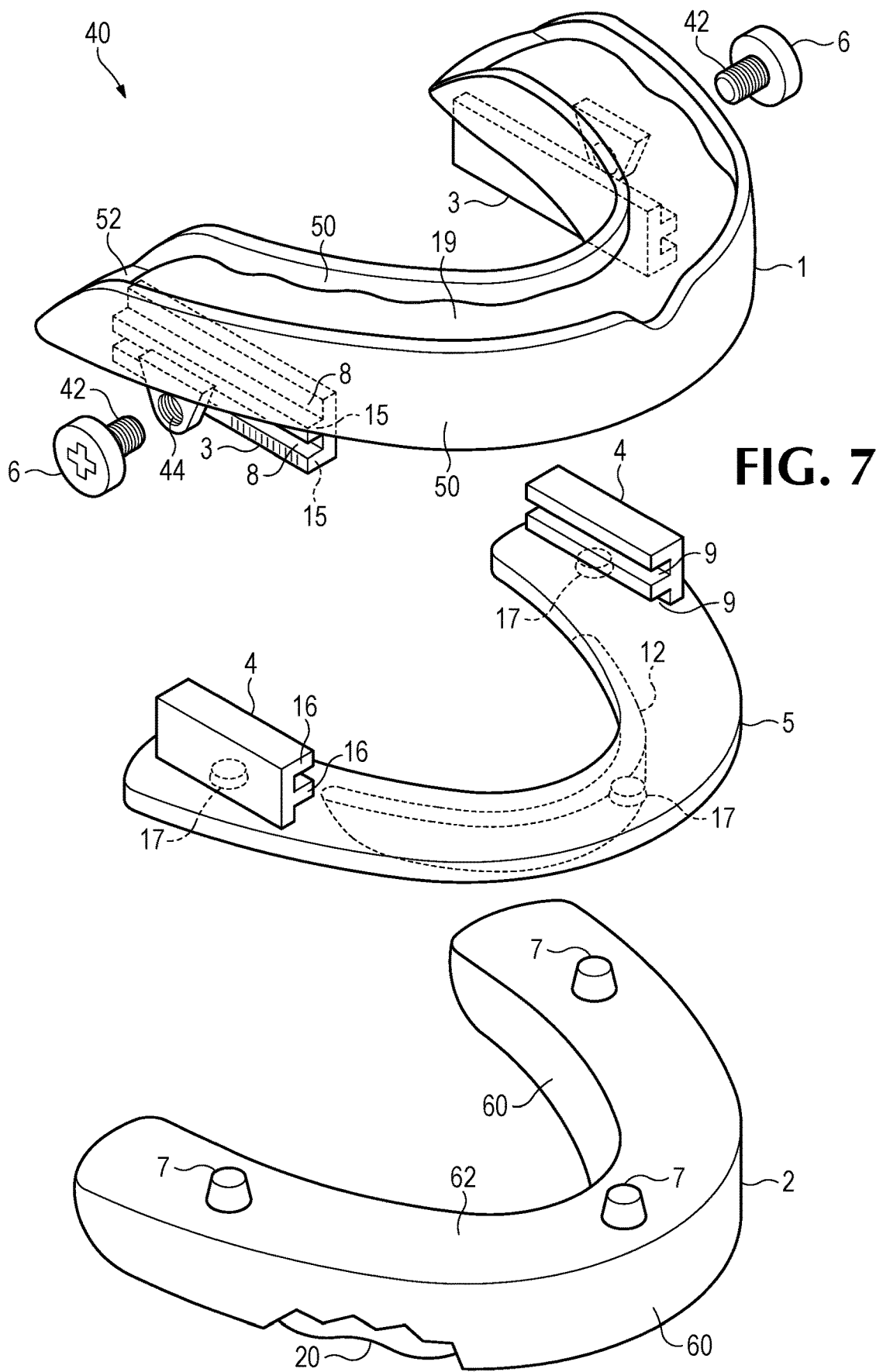
FIG. 7 is an exploded view of the snore and sleep apnea treatment dental appliance of FIG. 1.

Referring now to FIG. 7, locking pin 6 includes a knob portion, to be easily adjusted by a human user, and a threaded portion 42, that fits into threaded receptacle 44, by which means threaded portion 42 may be brought into contact with assembly 4, thereby locking the position of assembly 4, relative to assembly 3, and piece 5 in position relative to upper portion 1. In the embodiment shown, locking pin 6 is made to receive a phillips head screwdriver, but in other embodiments, pin 6 could receive an allen wrench, a slotted screwdriver or some other device.

More specifically, upper portion 1 and reflex inducing piece 5 fit together by a set of upper portion rails 15, defining linear spaces 8, into which reflex inducing piece rails 16 fit. Upper portion rails 15, fit into linear spaces 9, defined by reflex inducing piece rails 16. This permits forward and backward movement of reflex inducing piece relative to the upper portion 1, to be locked in place, as noted, by locking pins 6. It also permits differing vertical placements of the reflex inducing piece 5, by engaging the top rail 16, with either the top space 8, or the lower space 8.

Appliance 40 includes side walls 50 and a bottom wall 52 of upper portion 1, and side walls 60 and a top wall 62 of bottom portion 2. In a set of embodiments, the spaces defined by walls 50 and 52, and walls 60 and 62 are originally filled with a thermoplastic material 19 (in upper portion 1) and 20 (in bottom portion 2) having a softening temperature well below that of the softening temperature of the wall 50, 52, 60 and 62. The user is instructed to boil the appliance 40, thereby softening the thermoplastic material 19 and 20, insert the appliance 40 into the patient's mouth and to bite, thereby forming an impression of the patient's dentition into the thermoplastic 19 and 20. In one embodiment this is part of a process of forming a permanent appliance from measurements made using appliance 40. Walls 50 and 52 may be referred to as a "hard shell," and are referred to in this manner in the incorporated provisional application, as are walls 60 and 62.

Reflex-inducing piece 5 includes a downward projection 12 for making contact with the lower portion 2, which in turn pushes against the patient's dentition, inducing the mechanoreceptor reflex. To buffer the contact between piece 5 and portion 2, three resiliently deformable frustoconical shaped projections 7 are provided on the top of top wall 62. In one embodiment piece 5 is made with pits (not shown) matched to projections 7, so that the projections may fit into the pits, and provide a greater stability. In an alternative embodiment (not shown) projections are provided on the bottom of piece 5, and in one embodiment of this variety, matching pits are provided in top wall 62, to receive projections 7. In one version of the method of forming a dental imprint in the thermoplastic material 19 of the bottom portion 2, after this imprint is formed, projections 7 which did attach bottom portion 2 to piece 5, are broken, thereafter acting as shock absorbers and providing sliding contact between portion 2 and piece 5, for greater patient comfort.

As part of the process of forming measurements for a more permanent appliance, the user may use a recording and analysis app on their smart phone while sleeping, with appliance 40 held in the mouth. If snoring and or sleep apnea is detected, this provides an indication that the appliance 40 should be readjusted (or "titrated"), with reflex-inducing piece 5 moved to a further forward position, thereby pressing harder against the rearmost sidewall 60, and stimulating the mechanoreceptor reflex to move the lower jaw further forward, thereby further opening up the airway. If further forward movement is not enough to adequately reduce the snoring or improve the sleep apnea, the reflex-inducing piece 5 can be repositioned further down vertically with the top rail 16 fitting into the lower channel 8 of the number 3 assembly to increase the tongue space. If no snoring or sleep apnea is detected, the user may try adjusting the appliance 40, so that the piece 5 is retracted relative to the previous position, for greater patient comfort. When the furthest rearward position at which piece 5 can be moved, which effectively prevents snoring and apnea, has been determined, the appliance 40 may be sent to a lab, which will use the impression of the dentition formed in the thermoplastic, and the position of the reflex-inducing piece 5 to form a more permanent appliance, for treating sleep apnea on an ongoing basis.

In the method described above, one way in which a more permanent appliance can be formed is from digital printing from measurements taken from the temporary appliance 40. Alternatively, the patient's dentition may be measured directly, for example using an optical or laser instrument. In an alternative preferred embodiment, either a permanent or temporary dental appliance may be formed by digital printing, having the same essential configuration (except for the omission of the unneeded thermoplastic 19), including rails 15 and 16 and channels 8 and 9.

Referring now to FIGS. 8 and 9, in a further preferred embodiment, where the advancement of the reflex inducing piece 5 is made by choosing a reflex inducing piece 5 from a set of such pieces and fitting the chosen piece 5 into upper portion 1 in a predetermined physical relationship. In FIGS. 8 and 9, piece 5 is shown in conjunction with piece 2, but in a preferred embodiment, they are physically separate.

The disclosed embodiments are illustrative, not restrictive. While specific configurations of the dental appliance have been described, it is understood that the present invention can be applied to a wide variety of treatment types. There are many alternative ways of implementing the invention.

What is claimed is:

1. A method of providing a patient with a dental appliance adapted to treat sleep apnea by touching the front lower dentition, thereby stimulating the mechanoreceptor reflex, comprising:
   a) providing said patient with a temporary appliance, having:
      i. an upper portion adapted to engage with upper teeth of said patient;
      ii. a lower portion, adapted to touch lower teeth of said patient;
      iii. a reflex-inducing portion suspended from said upper portion, and having a downward projection adapted to contact the lower portion causing the lower portion to push against the lower front dentition of the patient, such that a mechanoreceptor reflex is induced to advance the lower jaw;
      iv. a user accessible adjustment actuator, which can be used advance or retract said reflex-inducing portion to place an adjusted amount of pressure against said lower portion, thereby causing said lower portion to place an adjusted amount of pressure against said lower teeth of said patient; and v. directing said patient to adjust said actuator, and thereby said appliance, as needed to treat sleep apnea, thereby creating an adjusted and titrated appliance; and b) receiving an adjusted appliance from said patient and producing a permanent appliance based on said adjusted and titrated appliance.

2. The method of claim 1, wherein said upper portion and said reflex-inducing portion are also adjustable in vertical displacement, and wherein said adjusted appliance also includes a vertical displacement between said upper portion and said lower portion that is used in producing a permanent appliance.

3. The method of claim 1, wherein said reflex-inducing portion is slidingly engaged to said upper portion, and wherein a locking pin temporary appliance includes a locking pin to selectively lock the position of said reflex-inducing piece to said upper portion.

4. The method of claim 1, wherein a set of differing reflex-inducing pieces is provided and wherein said reflex-inducing piece is slidingly engaged to said upper portion, and wherein said reflex-inducing piece is moved forward and back by selecting a different reflex-inducing piece from said set.

5. The method of claim 1, wherein said temporary appliance is also used to form an impression of said patient's dentition.

6. The method of claim 5, wherein said patient is instructed to boil said temporary appliance before wearing, and wherein boiling softens portions of said temporary appliance which are used to form impressions of said patient's teeth.

7. The method of claim 6 wherein the upper and lower portion contain thermoplastic contained in a shell of plastic that is not softened by the temperatures at or below 100° Celsius, and wherein the thermoplastic is softened by boiling and is used to form impressions of dentition.

8. The method of claim 1, wherein producing a permanent appliance based on said adjusted and titrated appliance is performed by digitally printing said permanent appliance based on said adjusted and titrated appliance.

9. A dental appliance adapted to treat sleep apnea in a patient, comprising:

a) an upper portion adapted to engage with the upper teeth of the patient;

b) a lower portion, adapted to engage with the lower teeth of the patient;

c) a reflex-inducing piece, suspended from said upper portion, and having a downward projection adapted to contact the lower portion causing the lower portion to push against the lower front dentition of the patient, such that a mechano-receptor reflex is induced to advance the lower jaw; and d) a reflex-inducing piece movement assembly, including a patient-accessible actuator, for moving said reflex-inducing piece alternately forward and backward, as chosen by said patient.

10. The dental appliance of claim 9, wherein said dental appliance includes a respective shell containing thermoplastic in both said upper and lower portion, and wherein when boiled said thermoplastic softens to form an impression of the respective dentition.

11. The dental appliance of claim 9, wherein said reflex-inducing portion is slidingly engaged to said upper portion.

12. The dental appliance of claim 11, wherein said dental appliance further includes a locking pin, which when tightened locks the position of said reflex-inducing piece to said upper portion.

13. The dental appliance of claim 11, wherein the reflex-inducing piece is chosen from a set of differing reflex-inducing pieces.

14. A dental appliance adapted to treat sleep apnea in a patient, comprising:

a) an upper portion adapted to engage with the upper teeth of the patient;

b) a lower portion, adapted to engage with the lower teeth of the patient;

c) a reflex-inducing piece, supported by said upper portion, and having a downward projection adapted to contact the lower portion causing the lower portion to push against the lower front dentition of the patient, such that a mechano-receptor reflex is induced to advance the lower jaw; and d) three deformable projections are arranged in a triangle between said lower portion and said reflex-inducing piece.

15. The dental appliance of claim 14, wherein said deformable projections are of a frustoconical shape.

16. The dental appliance of claim 14, wherein said reflex-inducing piece is position adjustable relative to said upper portion.

17. The dental appliance of claim 14, wherein said deformable projections are a part of said lower portion.

* * * * *